United States Patent
Schwarz (10) Patent No.: US 12,232,702 B2
(45) Date of Patent: *Feb. 25, 2025

(54) ENDOSCOPE WITH ROTARY DRUM AND OPERATING METHOD

(71) Applicant: KARL STORZ SE & Co. KG, Tuttlingen (DE)

(72) Inventor: Peter Schwarz, Tuttlingen (DE)

(73) Assignee: KARL STORZ SE & CO. KG, Tuttlingen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/456,689

(22) Filed: Nov. 29, 2021

(65) Prior Publication Data
US 2022/0175219 A1    Jun. 9, 2022

(30) Foreign Application Priority Data
Dec. 9, 2020    (DE) ...................... 10 2020 132 778.1

(51) Int. Cl.
*A61B 1/005*    (2006.01)
*A61B 1/00*    (2006.01)
(Continued)

(52) U.S. Cl.
CPC ........ *A61B 1/0057* (2013.01); *A61B 1/00004* (2013.01); *A61B 1/00096* (2013.01);
(Continued)

(58) Field of Classification Search
CPC ............ A61B 1/00018; A61B 1/00066; A61B 1/00073; A61B 1/00094; A61B 1/00096;
(Continued)

(56) References Cited

U.S. PATENT DOCUMENTS 3,896,793 A * 7/1975 Mitsui ................ A61B 1/00165
600/173
2002/0049367 A1* 4/2002 Irion ................ A61B 17/00234
600/173

(Continued)

FOREIGN PATENT DOCUMENTS

| EP | 1 759 629 A1 | 8/2005 |
| EP | 3 028 623 A1 | 10/2015 |
| WO | 2017/040692 A1 | 3/2017 |

*Primary Examiner* — Aaron B Fairchild
*Assistant Examiner* — Stephen Floyd London
(74) *Attorney, Agent, or Firm* — Eversheds Sutherland (US) LLP (57) ABSTRACT

An endoscope with a rotating drum or a rotation module, in particular for use as a sterile disposable instrument, having an elongate rigid and/or flexible shaft tube which at a distal end mounts the rotating drum, so as to be rotatable about at least one first axis of rotation, an optical imaging system being arranged in the rotating drum, with the at least one first axis of rotation running approximately transversely to a longitudinal axis of the shaft tube and with the endoscope having at least one control line for rotating the rotating drum. Here, the at least one control line of the rotating drum runs on an outer side/outer face of the shaft tube, and is fastened to the rotating drum at at least one lever distance (a) from the at least one first axis of rotation.

1 Claim, 9 Drawing Sheets

(51) Int. Cl.
*A61B 1/015* (2006.01)
*A61B 1/06* (2006.01)
*A61B 1/12* (2006.01)

(52) U.S. Cl.
CPC .......... *A61B 1/00103* (2013.01); *A61B 1/015* (2013.01); *A61B 1/06* (2013.01); *A61B 1/12* (2013.01)

(58) Field of Classification Search
CPC ............ A61B 1/00101; A61B 1/00105; A61B 1/00112; A61B 1/00114; A61B 1/00117; A61B 1/00119; A61B 1/00121; A61B 1/00124; A61B 1/00126; A61B 1/00128; A61B 1/0014; A61B 1/00183; A61B 1/0052; A61B 1/0053; A61B 1/0057; A61B 1/0125; A61B 1/015; A61B 1/018; A61B 1/05; A61B 1/051; A61B 1/053; A61B 1/0627; A61B 1/126; A61B 1/00098; A61M 2025/015; A61M 2025/0161
See application file for complete search history.

(56) References Cited

U.S. PATENT DOCUMENTS

| | | | |
|---|---|---|---|
| 2003/0032863 A1* | 2/2003 | Kazakevich | A61B 1/00105 600/173 |
| 2005/0234296 A1* | 10/2005 | Saadat | A61B 1/0008 600/173 |
| 2005/0234297 A1* | 10/2005 | Devierre | A61B 1/00087 600/129 |
| 2008/0234547 A1* | 9/2008 | Irion | A61B 1/00071 600/146 |
| 2009/0088631 A1* | 4/2009 | Dietz | A61B 90/37 600/424 |
| 2013/0096381 A1* | 4/2013 | Manohara | A61B 1/0676 600/109 |
| 2013/0242071 A1* | 9/2013 | Wada | G02B 23/2484 348/76 |
| 2014/0012080 A1* | 1/2014 | Wada | A61B 1/00183 600/109 |
| 2014/0249369 A1* | 9/2014 | Hanabusa | A61B 1/051 600/109 |
| 2015/0216402 A1* | 8/2015 | Ray | A61B 1/00096 600/109 |
| 2015/0359420 A1* | 12/2015 | Hatase | A61B 1/0055 600/110 |
| 2016/0015261 A1* | 1/2016 | Kishi | A61B 1/00091 600/109 |
| 2016/0073855 A1* | 3/2016 | Farr | A61B 1/0615 600/109 |
| 2017/0078583 A1* | 3/2017 | Haggerty | H04N 23/55 |
| 2017/0251908 A1* | 9/2017 | Surti | A61B 1/0684 |
| 2019/0357883 A1* | 11/2019 | Steinberg | A61B 8/4466 |
| 2021/0401270 A1* | 12/2021 | Sigmon, Jr. | A61B 1/31 |
| 2022/0248946 A1* | 8/2022 | O'Callaghan | A61B 1/0676 |

* cited by examiner

ENDOSCOPE WITH ROTARY DRUM AND OPERATING METHOD

TECHNICAL FIELD

The present invention relates to an endoscope with a rotating drum, in particular for use as a sterile disposable instrument, according to the preamble of claim 1 and to a method for operating the endoscope.

BACKGROUND OF THE INVENTION

Generic endoscopes are used as an observation instrument, in particular for medical operations, preferably for surgical operations, with said endoscopes being designed to have the smallest possible external dimensions for the purposes of a minimally invasive intervention. In addition to the use as an observation instrument, the endoscope can also be equipped with medical instruments and/or channels for fluid guidance, especially for laparoscopic, hysteroscopic or arthroscopic operations. Particularly in the case of simultaneous use of an optical imaging system and a work channel for instruments and/or channels for the fluid guidance, at least the functionality of the imaging system or the cross section of the work channel is restricted by the bounding and small external dimensions of a shaft tube of the endoscope. By way of example, in the case of this simultaneous use, there can be an embodiment of either an imaging system with a low resolution and/or restricted field of view or, alternatively, very small instruments with restricted options for the fluid guidance.

The shaft, or usually a shaft tube, of the endoscope can have a rigid or flexible embodiment or an embodiment that is flexible in sections. If a more detailed description is lacking, the shaft tube is understood to be a rigid and/or flexible shaft tube below.

An endoscope with a spherical rotating drum as an observation instrument with an increased field of view is known from EP 1 759 629 A1 of the applicant, and it accommodates an optical imaging system at least partially within the rotating drum on an elongate rigid shaft tube, wherein the rotating drum is pivotable about a first pivot axis which runs approximately transversely to a longitudinal axis of the rigid shaft tube and wherein the rotating drum is pivotable about at least one second pivot axis, which is spaced apart from the first pivot axis and which runs approximately transversely to the longitudinal axis of the rigid shaft tube. The endoscope has a control mechanism for controlling the pivot movement of the first and second pivot axis, said movement being driven by means of a gearing with gear wheels in the interior of the rigid shaft tube, preferably by means of a belt drive. As a result of the embodiment of the endoscope with a twice pivotable rotating drum it is possible to enlarge the field of view of the imaging system in particular, with however the control mechanism requiring the entire volume of the rigid shaft tube and hence not allowing a work channel to be arranged in the interior of the rigid shaft tube.

WO 2017/040692 A1 likewise discloses an endoscope with a spherical rotating drum on an elongate rigid shaft tube, especially for use as a disposable instrument, wherein the rotating drum is rotatably mounted in a bearing fork at a distal end of the rigid shaft tube and can be rotated in the interior of the rigid shaft tube by means of a control line. The rotating drum has an imaging system in its interior and is connected to electronic elements in the interior of the rigid shaft tube, wherein a fluid can be guided through the interior of the rigid shaft tube at the same time. In this embodiment of an endoscope with a rotating drum, a majority of the rigid shaft tube is occupied by the electronic elements of the imaging system and the control line.

EP 3 028 623 A1 of the applicant discloses an endoscope in which an instrument can be guided in the interior of the elongate rigid shaft tube together with an imaging system. In this case, the internal diameter of the rigid shaft tube is occupied almost entirely by the imaging system and the field of view is restricted as a result of the hermetic seal of the imaging system.

US 2015/0359420 A1 discloses for example an endoscope with a flexible shaft tube and a rotating drum, which is mounted in a sealed housing on a rigid distal end of the flexible shaft tube and which is controllable by means of a mechanical mechanism in the interior of the flexible shaft tube.

As mentioned previously, the external diameter of endoscopes, in particular of their shaft tube, is restricted for a minimally invasive medical intervention and the channels or work channels, provided in the interior of the shaft tube, for different functions such as guiding fluids, instruments or tools and the electronics for an imaging system at the distal end of the shaft tube must be split, preferably in space-saving fashion. Thus, combining the various functions is dispensed with entirely or in part in the cited prior art, or the respective functions are restricted. The installation space for the electronics of an imaging system or a sensor is restricted, especially in favor of using comparatively large work channels for fluid and/or instrument guidance, and so a small sensor with a low resolution is usually used for the imaging.

Medical applications, in particular, demand a sterile and autoclavable imaging system with electronic connectors, with the imaging system with electronic connectors and a control mechanism usually being hermetically sealed and therefore, as a result of the sealed housing, only being combinable to a restricted extent with further functions within the shaft tube in space-saving fashion.

SUMMARY OF THE INVENTION

The present invention is therefore based on the object of proposing an endoscope which facilitates the use of a large work channel in relation to the internal diameter of the shaft tube and which avoids the known problems from the prior art without restricting the field of view or the resolution of the imaging system in the process.

Further, it is an object to specify a method for operating the endoscope according to the invention.

This object is achieved by the features of independent claim 1 in respect of the endoscope.

Advantageous embodiments are the subject matter of the dependent claims.

According to the invention, an endoscope with a rotating drum or a rotation module, in particular for use as a sterile disposable instrument, having an elongate rigid and/or flexible shaft tube is proposed, which shaft tube at a distal end mounts the rotating drum preferably by means of a bearing fork, so as to be rotatable about at least one first axis of rotation, an optical imaging system being arranged in said rotating drum, the optical imaging system preferably comprising an electronic image recorder and/or an imaging optical unit and/or an illumination device, with the first axis of rotation running approximately transversely to the longitudinal axis of the shaft tube and with the endoscope having at least one control line for rotating the rotating drum preferably by way of a linear movement. Here, the at least one control line of the rotating drum runs on an outer side of the shaft tube, preferably so as not to restrict a work channel in the interior of the shaft tube and the internal diameter of the shaft tube, and is fastened to the rotating drum at a lever distance from the at least one first axis of rotation.

Within the scope of the invention, the rotating drum or the rotation module is understood in general terms to be an apparatus for receiving an imaging system; preferably, this is a pivotable or rotatable apparatus at a distal end of the shaft tube, and is therefore preferably referred to as rotating drum within the scope of the invention.

In this case, the invention has surprisingly recognized that the installation space for functional work channels in the interior of the shaft tube can be extended as a result of the external arrangement of the at least one control line. In this case, the work channel can be used in modular fashion for different or combined functions, for example for guiding a fluid or different fluids or a multiplicity of fluids, in particular in different flow directions, and/or for guiding instruments. In particular, the whole internal diameter of the shaft tube can be in the form of a work channel. Moreover, the external diameter can be reduced for the same work channel size, which shortens the healing process of a patient particularly in the case of medical operations since no wounds or smaller wounds arise and, overall, less volume is displaced by the endoscope.

Advantageously, the endoscope according to the invention allows different functions to be combined without restricting any of the functionalities in the process. Thus, it is possible to use a high-resolution imaging system with a large field of view without restricting the work channel size in the process. The use of the rotating drum with the imaging system, in particular, allows a relatively large field of view to be facilitated by pivoting the rotating drum using a control mechanism that has a relatively simple and robust embodiment.

Preferably, the endoscope is embodied as a disposable instrument such that it is preferably not necessary to hermetically seal the rotating drum with the bearing point and at least a portion of the bearing fork, in particular since the region of the bearing fork can only be disinfected to a limited extent. Therefore, the endoscope can preferably also be suitable for industrial applications.

According to a preferred embodiment, the at least one control line is windable along at least one winding curve preferably on the outer circumference of the rotating drum. As a result, the control mechanism can be constructed in particularly simple fashion and advantageously there is no need for gear wheels or transmissions and the mount thereof, which are susceptible to faults or require much maintenance.

It is further preferable for the at least one control line of the rotating drum to be embodied as a supply line for the imaging system, preferably as a flexible printed circuit board or as a cable, for electronic circuits in the interior of the rotating drum. As a result, the mechanical control, in particular pivoting by way of the control line, can also be realized in addition to the electrical or electronic control of the rotating drum.

The supply line can contain electronic circuits, in particular of an electronically adjustable imaging optical unit and/or of an electronic image recorder or sensor of the imaging system and/or of the illumination device, preferably with LEDs. Especially as a result of using the endoscope as a disposable instrument, the supply line need not be autoclavable and can be embodied with a small cross section. As a result of the simultaneous use of the supply line as a control line, it is particularly advantageously possible to dispense with a further control line for the rotation of the rotating drum.

Furthermore, it is preferable for the at least one control line of the rotating drum to comprise at least one first fluid line, which is windable on the rotating drum and which is designed to rinse an operation region with a fluid.

Within the scope of the invention, the fluid can preferably be understood to mean a liquid and/or a gas, wherein a sterile fluid, such as prepared oxygen as air/gas and a saline solution as a liquid is preferably utilizable in a medical use.

Particularly preferably, the at least one control line is guided in a recess, preferably with a protective collar, in the outer face of the shaft tube, the recess running parallel to the longitudinal axis of the shaft tube. As a result, the at least one control line is guided in space-saving and interlocking fashion on the outer side of the shaft tube in order, firstly, to protect the at least one control line from external mechanical influences and in order, secondly, to prevent a risk of injury or clamping of tissue during an operation.

Reset means, preferably in the form of a torsion spring in the bearing point of the rotating drum, are preferably arranged on the rotating drum for the control of the rotating drum. Here, the torsion spring acts counter to a mechanical moment of the tensioned control line in order to return a pivoted rotating drum to an initial position. Thus, the torsion spring preferably acts counter to an operation of the control line in such a way that a compression force need not be applied to the control line for the purposes of a rotation of the rotating drum, in order to allow the use of a flexible control line.

As an alternative or in addition thereto, the rotating drum can be returnable by a further control line on the opposite side and/or also be operable by means of a compression force by way of a dimensionally stable control line or a type of Bowden cable or a type of control rod or toothed rack.

Further alternatively, the further control line can preferably be in the form of a wire, wherein a return means, preferably a spring, in particular a helical spring, is preferably fastened in a handle for returning the rotating drum.

Preferably, provision can be made for the work channel to comprise at least one second fluid line, including preferably an air line and/or preferably a liquid feed line and a liquid extraction line in modular fashion. Especially since the imaging system with the supply line is not arranged within the shaft tube, a plurality of channels, such as the air line together with the liquid feed line and the liquid extraction line, can be provided within the shaft tube in particular. A type of overshaft around the shaft for fluid guidance, which increases the external diameter of the shaft tube, is advantageously not required. The functionality of the at least one second fluid line may comprise cleaning the optics and/or temperature-control for/cooling of the rotating drum and/or rinsing and insufflating a fluid in an operation region. Cooling the rotating drum is required in particular on account of a development of heat during operation of the electronic components of the imaging system with an electronic image recorder and/or illumination device.

In general, the fluid line can be used for temperature control of the shaft tube and the rotating drum. As an alternative to cooling, it may alternatively also be necessary to preheat the imaging system to the expected ambient temperature in an operation region prior to an operation. Usually, an increase in the ambient temperature is to be expected and preheating can prevent the imaging optical unit of the imaging system steaming up.

Advantageously, the air line is used in a dry operation region to dry the rotating drum following a cleaning of the optical unit and/or to cool the rotating drum and the electronic components of the imaging system.

In a dry environment of the endoscope, the work channel preferably has an air line, a liquid feed line and a liquid extraction line as at least one second fluid line. The optical unit of the endoscope is cleaned in a dry operation region, preferably in a cleaning position in which the rotating drum is rotated such that the field of view is aligned with the distal end of the shaft tube and the work channel. In this cleaning position, the imaging system can be rinsed with a rinsing liquid from the liquid supply line, wherein the rinsing liquid is removable via the liquid extraction line and this can minimize rinsing liquid leaking into a dry operation region. The rinsing liquid can preferably be removed from the imaging system using the air line in order to prevent a disturbance of the field of view of the imaging system by the formation of drops. Further preferably, the liquid supply line, and preferably the air line, too, can be embodied as a spray nozzle in order to improve the cleaning effect.

For a watery or wet operation region or environment of the endoscope, the liquid supply line and the liquid extraction line are preferably arranged in the work channel in order to flow around and control the temperature of the rotating drum on the back side, and in order to rinse the operation region. For rinsing the medical operation region, provision is preferably made for the shaft tube to have holes and/or an opening, preferably slot-shaped opening, of the work channel on the circumferential side at a distal end, in order to connect the at least one second fluid line, preferably the liquid extraction line, to the operation region and in order to be able to remove a rinsing fluid from the operation region. In particular, the shaft tube is open behind the rotating drum in order to ensure a free emergence of the rinsing fluid, in particular rinsing water.

Preferably, the work channel is designed to receive at least one instrument and/or contains at least one instrument in order to be able to carry out preferably medical operations in the operation region and, in particular, in the field of view of the imaging system. In this case, the at least one instrument has a controllable tool at a distal end, for example a scissors-type cutting tool or punching tool. The receptacle of the at least one instrument can be provided in addition or as an alternative to the at least one second fluid line. As a result of the external control line and, in particular, the external feed of the imaging system, the relatively large work channel can be utilizable for at least one instrument and, at the same time, a multiplicity of second fluid lines.

In a development, the shaft tube is open on an upper section, the at least one first control line being guided on an opposite lower section in order to adjust/bend a preferably flexible instrument in a direction perpendicular to the longitudinal axis of the shaft tube and into the open upper section. As a result, the instrument, in particular functional parts and tools at the distal end of the at least one instrument, can be brought into the operation region and the operation region can be tracked at the same time by the imaging system within the rotating drum.

Especially for the use of the endoscope with the at least one instrument, provision is preferably made for the bearing fork to be fastened to the shaft tube in a manner pivotable about a second axis of rotation and for the work channel to be open along the longitudinal axis in a pivoted state of the bearing fork in order to guide the at least one instrument, in particular, from the work channel into an operation region, the bearing fork preferably being controllable by way of a second control line. The second control line is preferably likewise guided on the outer side of the shaft tube in order not to restrict the work channel in the interior of the shaft tube. Using this embodiment, a rigid instrument, in particular, is guidable into the operation region in a manner parallel to the longitudinal axis of the shaft tube. Moreover, by rotating the rotating drum about the second axis of rotation, a preferably flexible instrument is bendable in a direction perpendicular to the longitudinal axis of the shaft tube. In addition to guidance of the at least one instrument, the pivotable bearing fork advantageously facilitates an extended field of view of the imaging system, also for example behind obstacles or corners or a view along an outer side of the shaft tube. Thus, for example, even the guidance function of the at least one control line along the shaft tube is able to be monitored by means of the imaging system. Furthermore, rinsing or extraction of a fluid from the operation region can be promoted by way of the open work channel.

Preferably, the external diameter of the shaft tube is 3 mm to 6 mm, with preferably the rotating drum not exceeding this external diameter. Such shaft tubes are suitable for a multiplicity of non-invasive medical operations.

In a further preferred embodiment, a plurality of control lines are windable on different winding curves along the circumference of the rotating drum, in particular with different distances from the axis of rotation in order to carry out different rotational adjustments of the rotating drum in the case of the same adjustment travel of the control line. In particular, the adjustment travel parallel to the longitudinal axis of the shaft tube and the different rotational adjustments can lead to predefined viewing directions of the imaging system or to different rotational speeds, wherein, in the case of the same adjustment travel of the control line, the rotational adjustment of the rotating drum reduces with decreasing distance from the first axis of rotation of the rotating drum. The tensile force required for the rotational adjustment can also be set by the different distances.

Particular preferably, the different winding curves are arranged in steps along the first axis of rotation on the circumference of the rotating drum, wherein the winding curves preferably are arranged in the direction of the outer sides of the rotating drum with decreasing distance from the first axis of rotation.

The invention also relates to a method for operating an endoscope, in particular an endoscope as described above, so as to control a rotating drum with an imaging system, preferably with an electronic image recorder and/or an imaging optical unit and/or an illumination device, at least one control line on an outer side/outer face of a shaft tube of the endoscope and a work channel in the interior of the shaft tube being arranged in non-restrictive fashion and being fastened to the rotating drum at at least one lever distance from an at least one first axis of rotation and the at least one control line subsequently being pulled or pushed in order to rotate the rotating drum.

In a development, the method is used to clean the endoscope, preferably a field of view of the imaging system, wherein in a first step the rotating drum is rotated from an observation position for an operation region to a cleaning position, in which the field of view is aligned with the distal end of the shaft tube and the work channel, and wherein the cleaning method described below is particularly suitable for endoscopes in a dry environment or dry operation region since leakage of rinsing liquid into an operation region can be minimized. In a second step, the imaging system and/or the imaging optical unit and/or the illumination device is/are rinsed, especially in the field of view, using a preferably aqueous rinsing fluid from the at least one second fluid line, preferably a liquid feed line with a spray nozzle. Preferably, the aqueous rinsing fluid can be aspirated by means of a further second fluid line, preferably a liquid extraction line, in order to minimize the leakage of rinsing fluid into an operation region. In the process, the rotating drum can be pivoted in order to clean the entire field of view. In a preferred third step, the preferably aqueous rinsing fluid is removed by means of a fluid flow, preferably an air flow, from an air line or a further second fluid line and the field of view of the imaging system is dried in this way. This step is required, in particular, if the endoscope is used in a dry operation region. In a fourth step, the rotating drum is rotated back into the observation position, preferably the observation position from the first step.

In a further embodiment of the method, an endoscope with a pivotable bearing fork is operated, wherein, in a first step, the shaft tube, at least the distal end of the shaft tube, is guided into an operation region and, in a second step, the bearing fork is pivoted about a second axis of rotation, at least until the rotating drum exposes the work channel along a longitudinal axis of the shaft tube. In a third step, an at least one instrument is guided from the work channel, in particular into the medical operation region. Subsequently and in a preferred fourth step, the rotating drum is pivoted by means of the control line about a first axis of rotation in order to track the at least one instrument in the operation region with a field of view of the imaging system and image said instrument for an operator. In a fifth step, the bearing fork can be pivoted about a second axis of rotation in order to move or bend the at least one instrument and align the latter with a defined operation region.

BRIEF DESCRIPTION OF THE DRAWINGS

Further advantages and details of the invention arise from the following description of preferred embodiments of the invention and on the basis of purely schematic drawings.

In detail:

FIG. 1a, FIG. 2a: shows a side view of the endoscope as per FIG. 1a, FIG. 2b: shows a longitudinal section of the endoscope as per FIG. 2a in a plane perpendicular to the first axis of rotation of the rotating drum, FIG. 4a, FIG. 5a: shows a longitudinal section of the endoscope as per FIG. 2b with a rotatably mounted bearing fork and an instrument, FIG. 7b: shows a perspective view of the endoscope as per FIG. 1a.

The same elements or elements with the same function have been provided with the same reference signs in the figures.

DETAILED DESCRIPTION

Figure 1A:
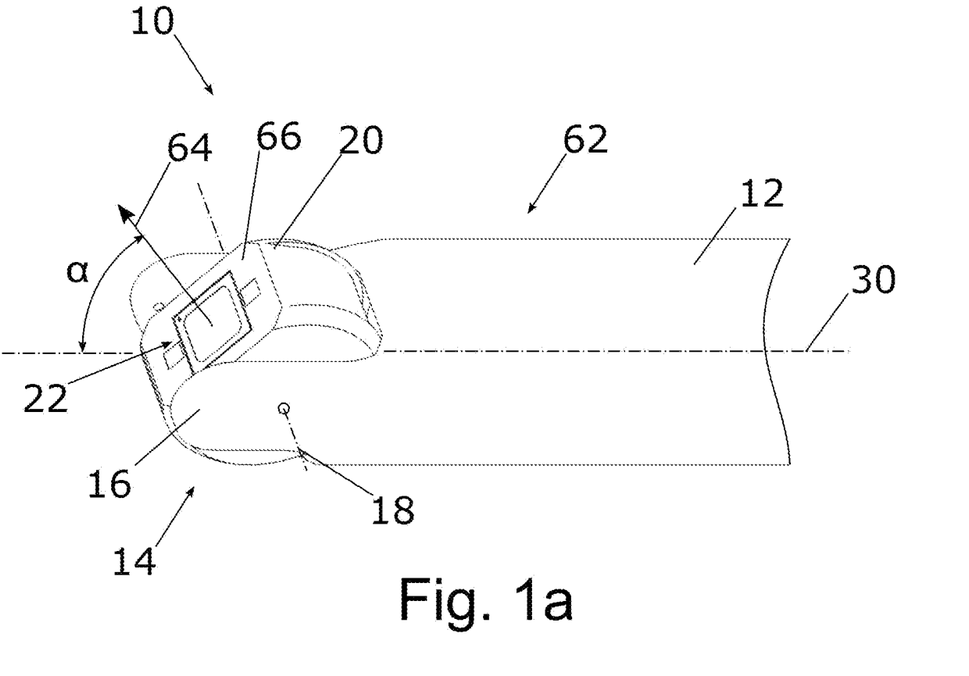
FIG. 1a: shows a perspective view of an upper side of a distal end of an endoscope having a rotating drum and a control line.

FIG. 1a illustrates an endoscope 10 with a rotating drum 20 on a distal end 14 of an elongate rigid shaft tube 12, wherein the rotating drum 20 is mounted at the distal end 14 of the shaft tube 12 by means of a bearing fork 16 so as to be rotatable about a first axis of rotation 18. An optical imaging system 22, which preferably comprises an electronic image recorder 24, an imaging optical unit 26 and an illumination device 28 as shown in detail in FIG. 2b, is arranged in the rotating drum 20. The rotating drum 20 is illustrated from an upper side 62 of the shaft tube 12, wherein a viewing direction 64 of the imaging system 22 is pivotable through an angle α with respect to the longitudinal axis 30 and the bearing fork 16 does not restrict the viewing direction 64 of the imaging optical unit 26. By pivoting the rotating drum 20, and hence the viewing direction 64, it is possible to cover an angle α of preferably more than 130° and an observation region β' as per FIG. 2b. By rotating the shaft tube 12 about the longitudinal axis 30, it is possible to extend the observation region β'. With a flexible distal end 14 of the shaft tube 12, as per FIG. 6, the entire operation region around the endoscope 10 is observable.

Figure 1B:
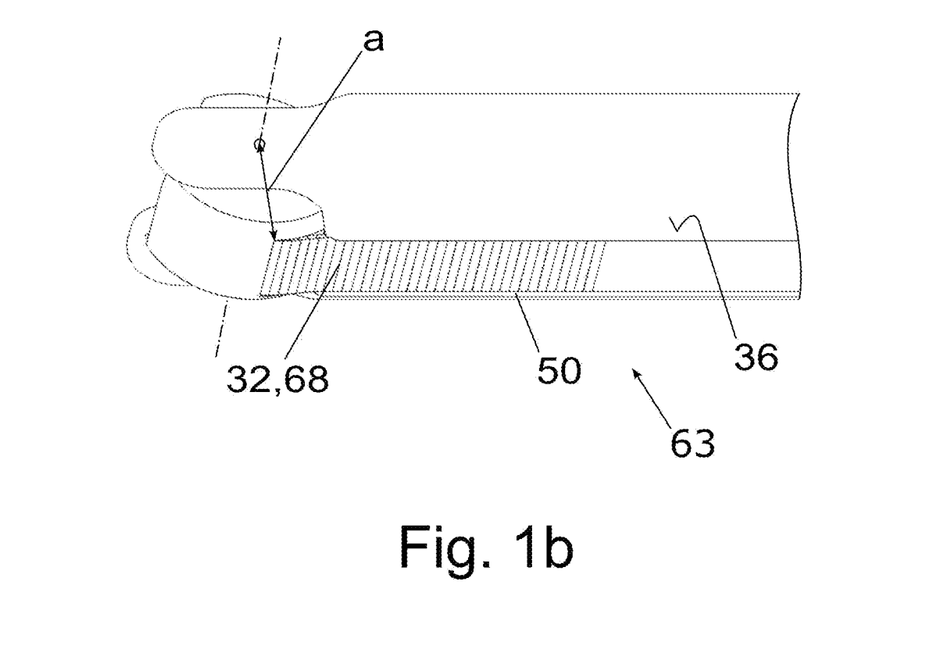
FIG. 1b: shows a perspective view of a lower side of the endoscope as per

The first axis of rotation 18 runs approximately transversely to a longitudinal axis 30 of the shaft tube 12, wherein the endoscope 10, as illustrated in FIG. 1b, has at least one, preferably one, control line 32 on a lower side 63 of the shaft tube 12. This at least one control line 32 is guided on an outer side 36 of the shaft tube 12 and fastened to the rotating drum 20 at a lever distance a from the first axis of rotation 18. The rotating drum 20 is rotatable, preferably by way of a linear movement of the at least one control line 32 parallel to the longitudinal axis 30 of the shaft tube 12.

Figure 6:
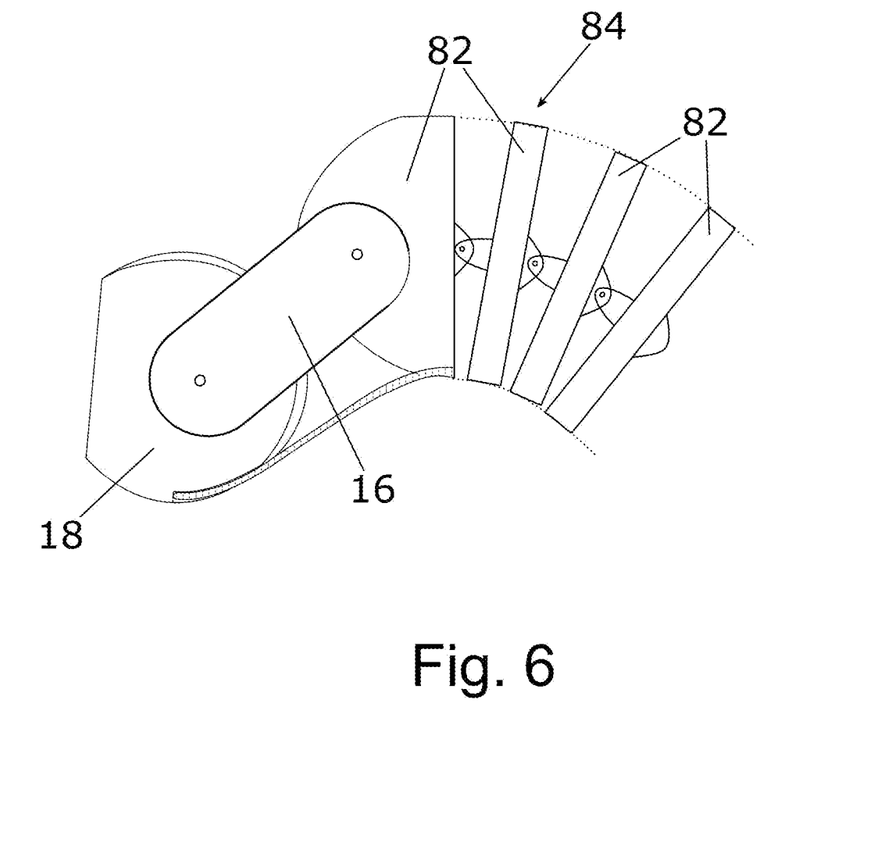
FIG. 6: shows a side view of an endoscope with a pivotable bearing fork as per FIG. 5a with a flexible shaft tube.

As an alternative, or in sections, the shaft tube 12 as per FIG. 6 can also be flexibly equipped, preferably at the distal end 14, with a multiplicity of steering members 82 and can be pivotable by means of control lines, not shown in any more detail, at an outer edge 84 of the steering members 82.

As shown in FIG. 2b, a work channel 34 in the interior of the shaft tube 12 and preferably the internal diameter of the shaft tube 12 are not restricted by the at least one control line 32.

The rotating drum 20 preferably has a spherical or cylindrical embodiment, with the rotating drum 20 preferably being flattened in a direction perpendicular to a viewing direction 64 of the imaging system 22 in order to receive the imaging optical unit 26 and the illumination device 28, preferably in the form of two LEDs, in a flattened region 66.

The at least one control line 32 is preferably windable on at least one winding curve 38 along the outer circumference of the rotating drum 20. Particularly preferably, the at least one control line 32 is windable such that the rotating drum 20 is rotatable from a viewing direction 64 along the longitudinal axis 30 of the shaft tube 12 through at least an angle α of 0° to 180° and hence the viewing direction 64 is alignable in the interior of the shaft tube 12 and a work channel 34. The viewing angle β of the imaging system 22 is preferably 50° to 70°, particularly preferably 60°. As a result, a preferred observation region β', in which the imaging system with a viewing angle β can record an operation region by pivoting the rotating drum 20 through an angle α, is between −35° and 215°, particularly preferably between −30° and 210°, wherein the angle of the observation region β', just like the angle α, relates to a 0° direction along the longitudinal axis 30 of the shaft tube 12. For the purposes of pivoting the rotating drum 20, the at least one control line 32 has an at least partly flexible embodiment, as indicated in FIG. 1b by transverse lines, in order to wind said control line on the at least one winding curve 38 of the rotating drum 20. In this case, the at least one winding curve 38 along the outer circumference can preferably have a circular or oval embodiment.

Particularly preferably, the at least one control line 32 of the rotating drum 20 forms a supply line for the imaging system 22, which preferably is embodied as a flexible printed circuit board 68 illustrated in FIG. 1b, for supplying electronic circuits in the interior of the rotating drum 20, for example the electronic image recorder 24 and/or an electronically adjustable imaging optical unit 26 and/or the illumination device 28. Particularly when using the flexible printed circuit board 68 as a control line 32, the corresponding winding curve 38 is designed such that the bending radius is greater than 0.5 mm. Alternatively, the imaging system 22 can also be electrically supplied by way of a cable 71, as illustrated in FIG. 2d.

Figure 2A:
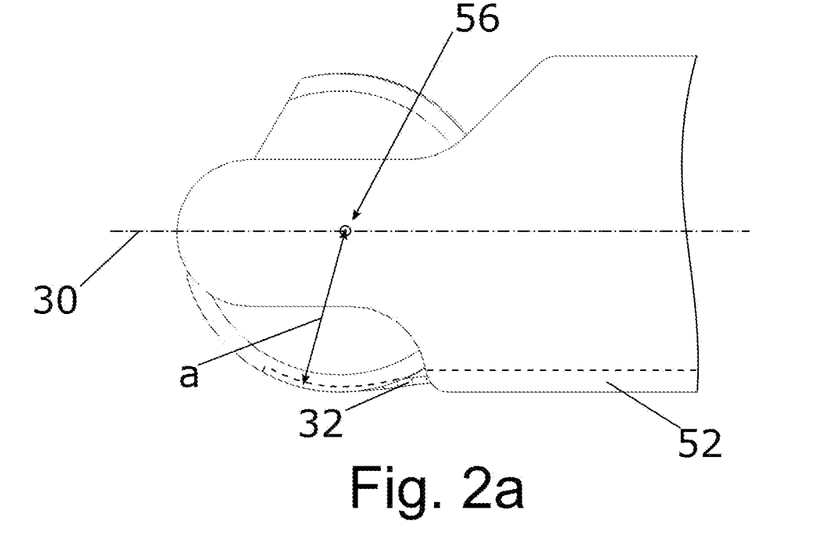
Figure 2B:
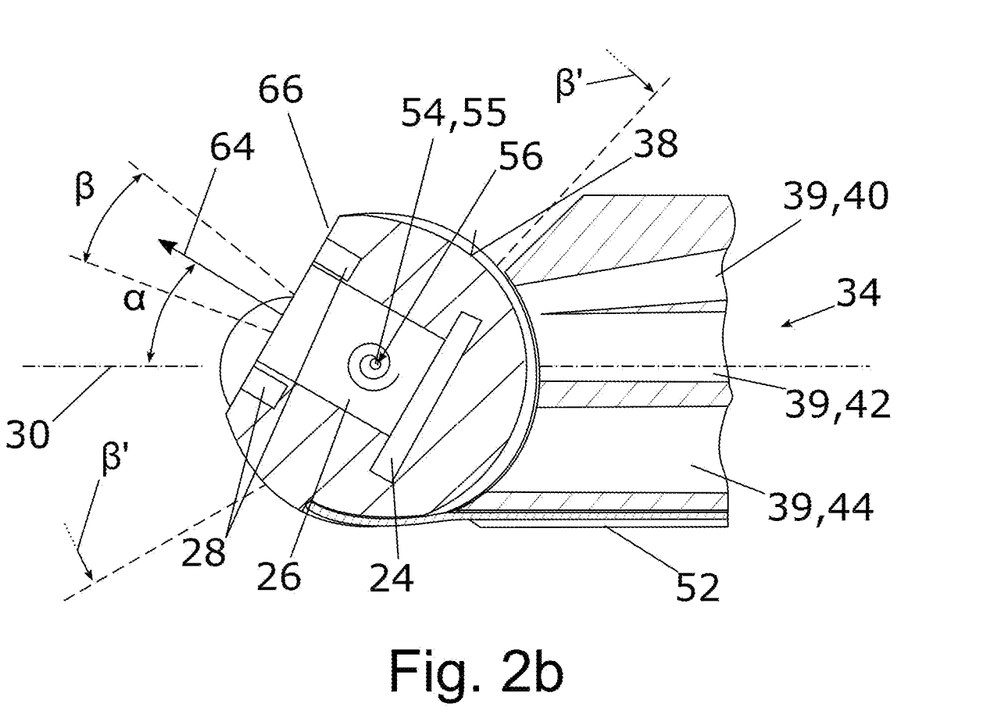
Figure 2C:
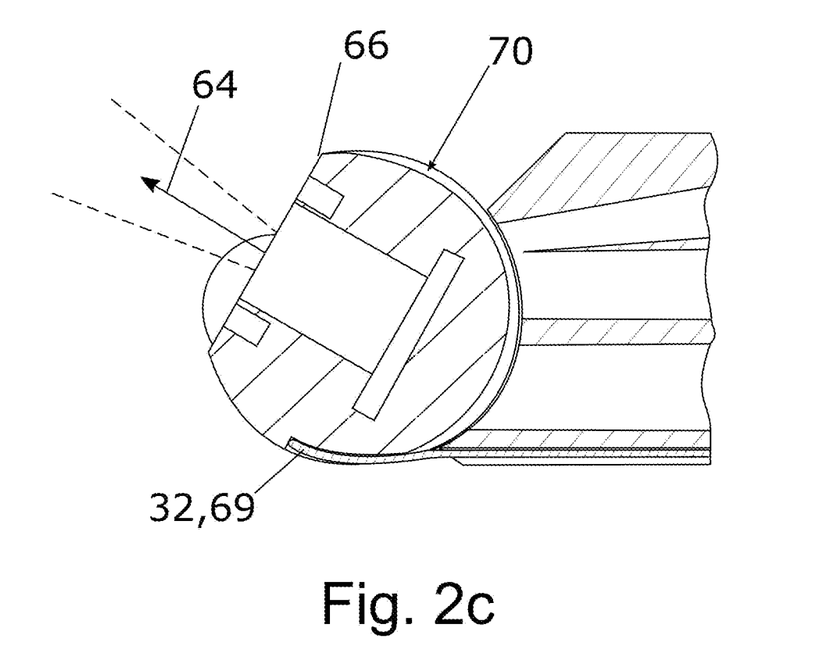
FIG. 2c: shows a longitudinal section of the endoscope as per FIG. 2b with a liquid line as a control line of the rotating drum.
Figure 2D:
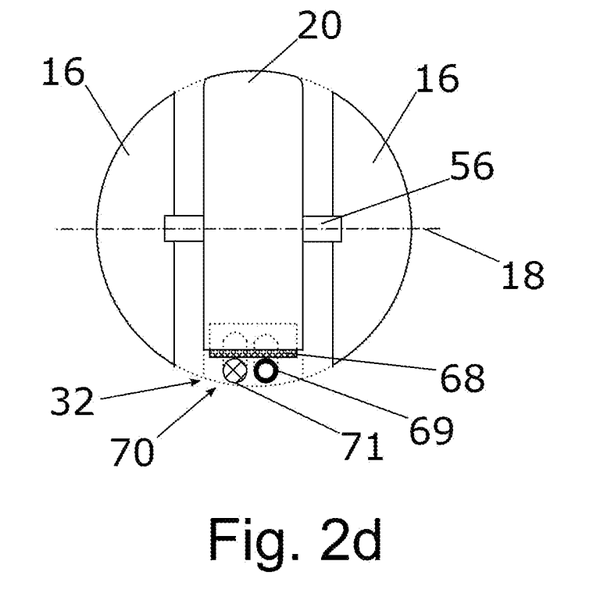
FIG. 2d: shows a plan view of the distal end of the endoscope in the longitudinal direction of the endoscope.

Furthermore, provision can be made for the at least one control line 32, as illustrated in FIG. 2c and FIG. 2d, to comprise at least one first fluid line 69. Here, this at least one first fluid line 69 is preferably provided in addition to an electronic supply line of the imaging system 22 and is windable on the winding curve 38; see FIG. 2d.

The at least one control line 32 is guided on the circumference of the rotating drum 20 in interlocking fashion, preferably in a depression 70, as per FIG. 2c and FIG. 2d, so that said control line is protected but at the same time the external diameter of the rotating drum 20 is not increased further, and so injury to tissue in an operation region can also be reduced.

As illustrated in FIG. 1b, FIG. 2a or FIG. 2b, the at least one control line 32 is guided in a recess 50 on the outer side 36 of the shaft tube 12, with the cutout 50 preferably running parallel to the longitudinal axis 30 of the shaft tube 12 and thus forming a protective collar 52, preferably in the region of the distal end 14 of the shaft tube 12. As a result, the at least one control line 32 is protected and injury of tissue in an operation region as a result of the movable control line 32 is prevented. Preferably, the protective collar 52 prevents the at least one control line 32 from being able to detach from the outer side 36 of the shaft tube 12 in a direction perpendicular to the longitudinal axis 30.

Preferably a torsion spring 55 as a reset means 54 is arranged in the region of the bearing point 56, as per FIG. 2b, for the purposes of resetting a rotated rotating drum 20, wherein the torsion spring 55 preferably keeps the rotating drum 20 in a cleaning position with an angle α of approximately 180° between the viewing direction 64 and the longitudinal axis 30 of the shaft tube 12.

Alternatively, the rotating drum 20 is also able to be reset by means of a second control line, not shown, on the upper side 62 of the shaft tube 12, or the control line 32 is guided in dimensionally stable fashion and in the recess 52, like a Bowden cable with a supporting sleeve, such that the control line 32 is also adjustable by means of a compression force.

Preferably at least one second fluid line 39, preferably an air line 39, 40 and/or preferably a liquid feed line 39, 42 and a liquid extraction line 39, 44, is arranged in the work channel 34 of the shaft tube 12. The air line 39, 40 and the liquid lines 39, 41, 44 are illustrated in FIG. 2b and FIG. 3b. In an observation position of the rotating drum 20, as per FIG. 2b, the at least one second fluid line 39 can be used for back-side cooling/temperature control of the imaging system 22.

Figure 3A:
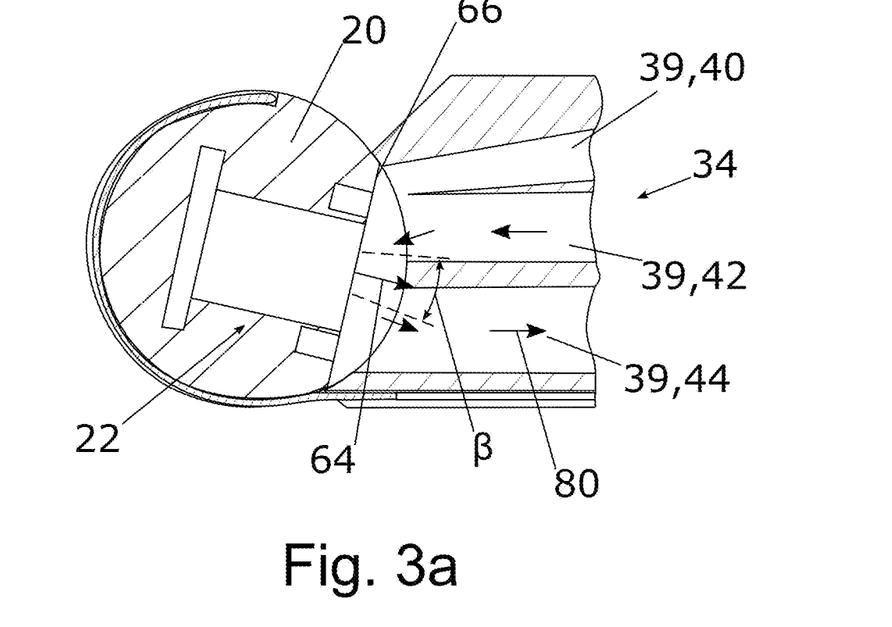
FIG. 3a: shows a longitudinal section of the endoscope as per FIG. 2b with a rotating drum in a cleaning position.
Figure 3B:
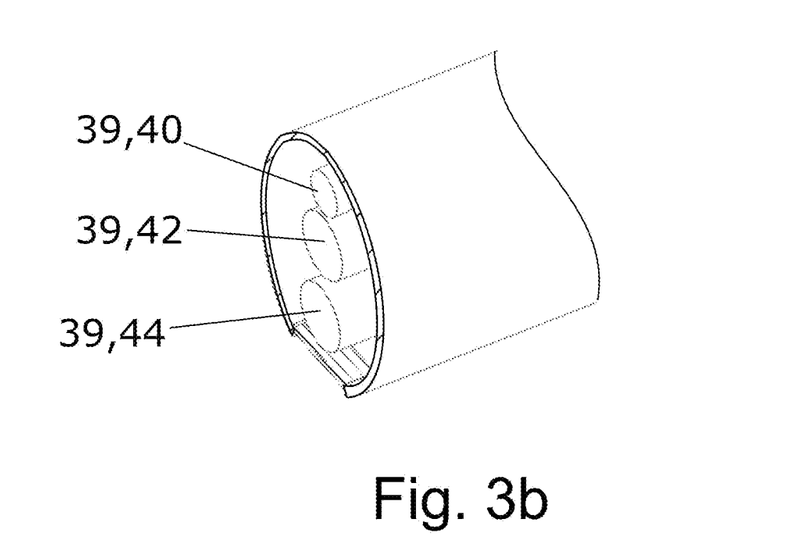
FIG. 3b: shows a cross section of the shaft tube as per FIG. 3a, perpendicular to the longitudinal axis of the shaft tube.

Especially for cleaning the imaging system 22 of endoscopes 10 in a dry operation region, the rotating drum 20 is preferably rotatable into a cleaning position as per FIG. 3a, wherein the rotating drum 20 with the viewing direction 64 is inclined in the direction of the work channel 34. In this cleaning position, contamination is preferably able to be rinsed from the flattened region 66 of the rotating drum 20, and hence the field of view β of the imaging system 22 is cleanable, preferably by means of an air line 39, 40 in combination with the liquid feed line 39, 42. Preferably, the rinsing fluid is a rinsing liquid from the liquid feed line 39, 42 for rinsing the imaging system 22, wherein the rinsing liquid is removable by means of the liquid extraction line 39, 44, and hence a leakage of rinsing liquid into a dry operation region can be minimized. Preferably, the air line 39, 40 is used to remove the rinsing liquid from the imaging system 22 and the flattened region 66 in order to prevent a disturbance in the field of view β of the imaging system 22 by drop formation. Further preferably, the liquid feed line 39, 42 and preferably also the air line 39, 40 can be designed as a spray nozzle in order to improve the cleaning effect.

Figure 4A:
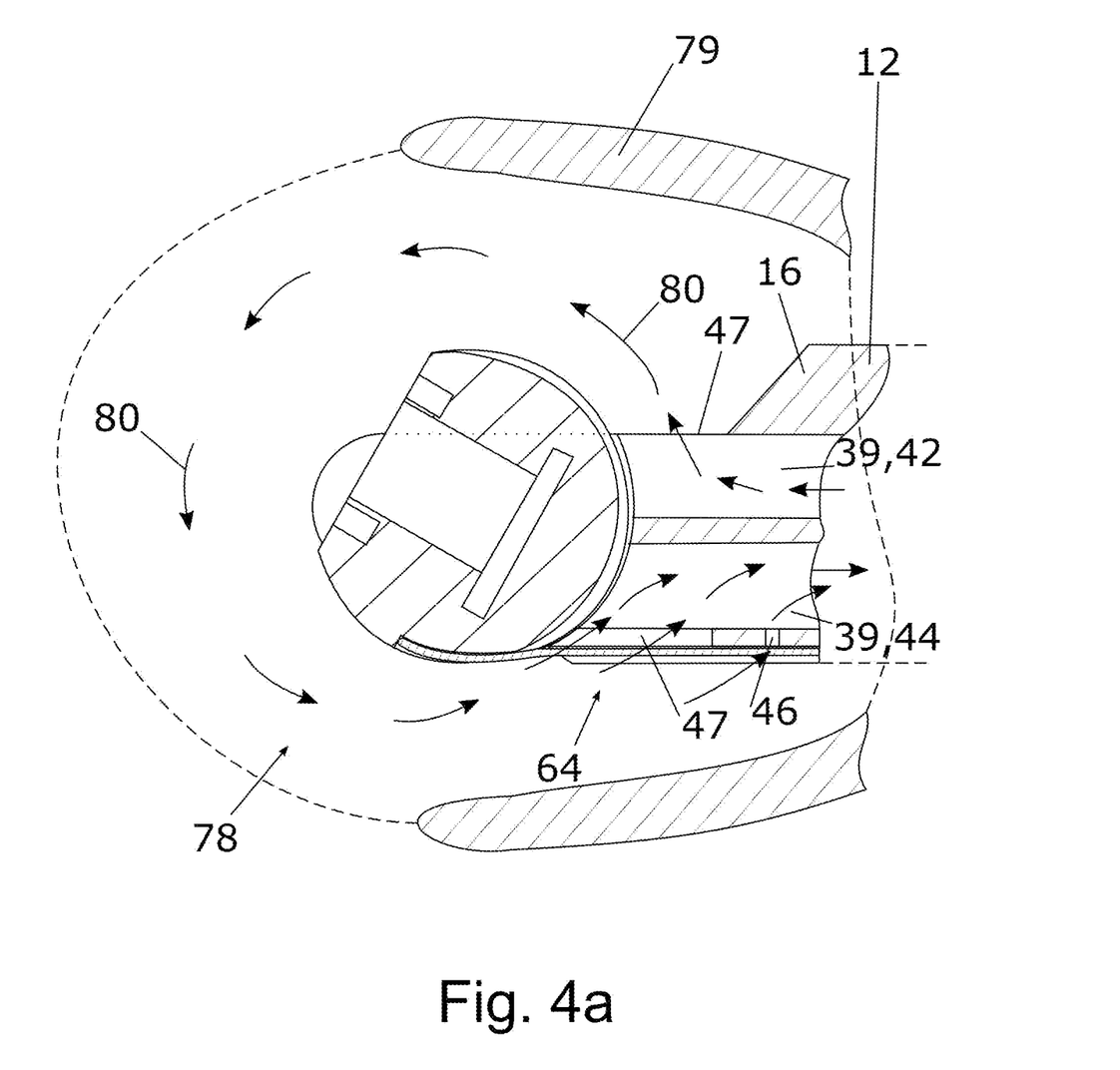
FIG. 4a: shows a longitudinal section of the endoscope as per FIG. 2b with a hole for extracting liquid.
Figure 4B:
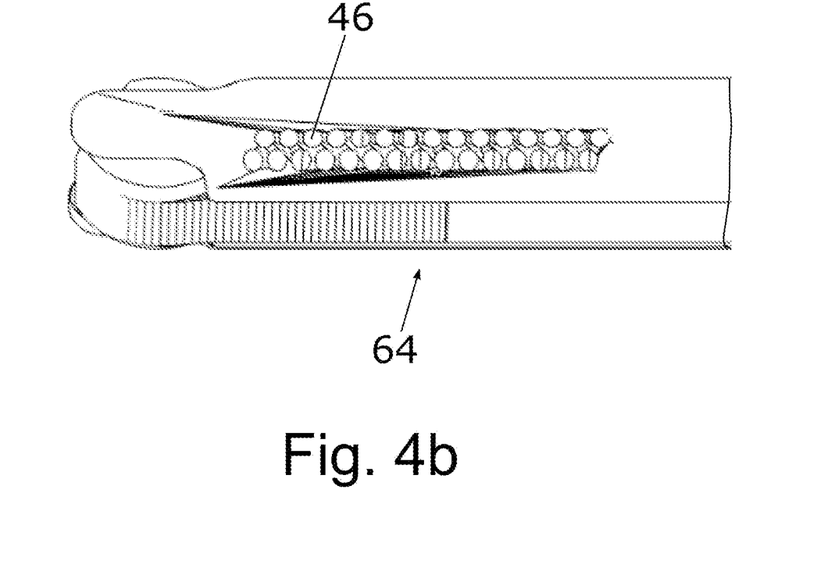
FIG. 4b: shows perspective view of an endoscope as per FIG. 1a with holes for extracting liquid.
Figure 4C:
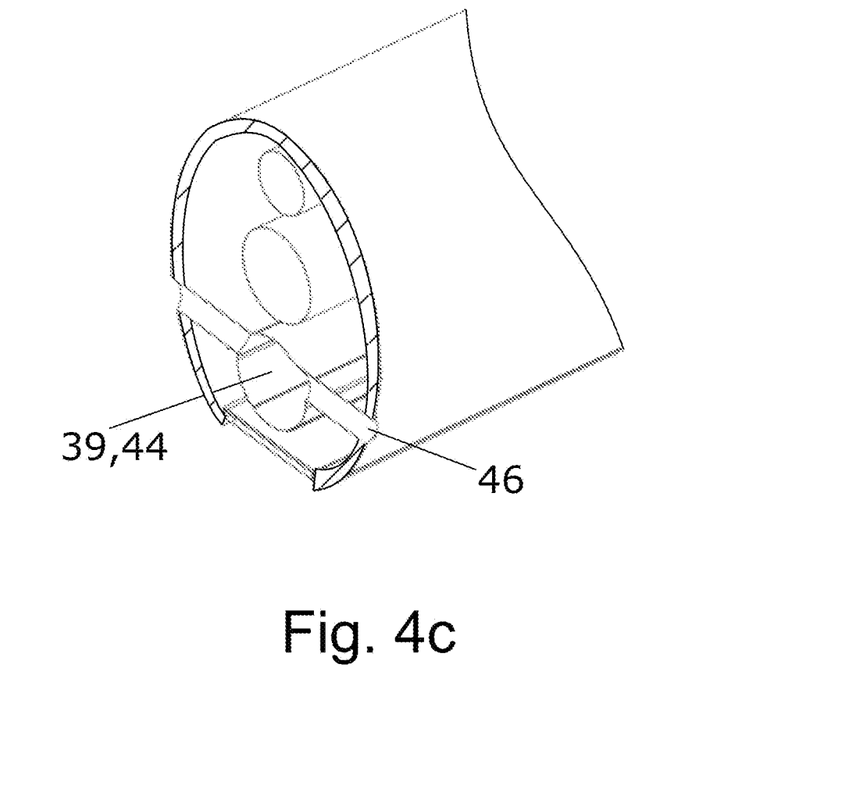
FIG. 4c: shows a cross section of the shaft tube as per FIG. 3b with holes as per

Preferably for endoscopes 10 with wet ambient conditions or in a wet operation region, the at least one second fluid line 39 can be used to rinse an operation region in addition to the back-side cooling and the cleaning of the rotating drum 20, in particular in order to rinse the operation region in the viewing direction 64 of the imaging system 22 in an observation position. To this end, a sterile and physiological rinsing fluid is preferably used for a medical application. To remove a rinsing fluid from an operation region, use is preferably made of a liquid extraction line 39, 44 with at least one hole 46 on the circumferential side or a slot-shaped opening 47 at the distal end 14 of the shaft tube 12, as illustrated in FIGS. 4a to FIG. 4c. The holes 46 and the opening 47 connect the liquid extraction line 39, 44, preferably on the lower side 64 of the shaft tube 12, to the operation region. Particularly for a bubble-shaped operation region 78 with tissue 79 to be operated, as per FIG. 4a, it is possible to rinse around the rotating drum 20 in a flow direction 80, wherein the circumferential holes 46 and the opening 47 promote the extraction of the rinsing fluid from the bubble-shaped operation region 78. Preferably only the liquid lines 39, 42, 44 are required for this rinsing use since an air line 39, 40 is preferably not required in a wet operation region and the imaging system 22 is able to be cleaned at the same time as the operation region is rinsed, without needing to be pivoted into a cleaning position in the process.

As an alternative or in addition thereto, it is also possible for the distance between the rotating drum 20 and the shaft tube 12, and hence the opening 47, to be increased in order to facilitate access to the liquid extraction line 39, 44 in FIG. 4a.

Furthermore, it is preferable for the shaft tube 12, in particular the bearing fork 16, to also have an opening 47 on the upper side 62 in order to open the shaft tube 12 behind the rotating drum 20 and thus ensure a clear emergence of rinsing fluid, in particular from the liquid feed line 39, 42.

Figure 5A:
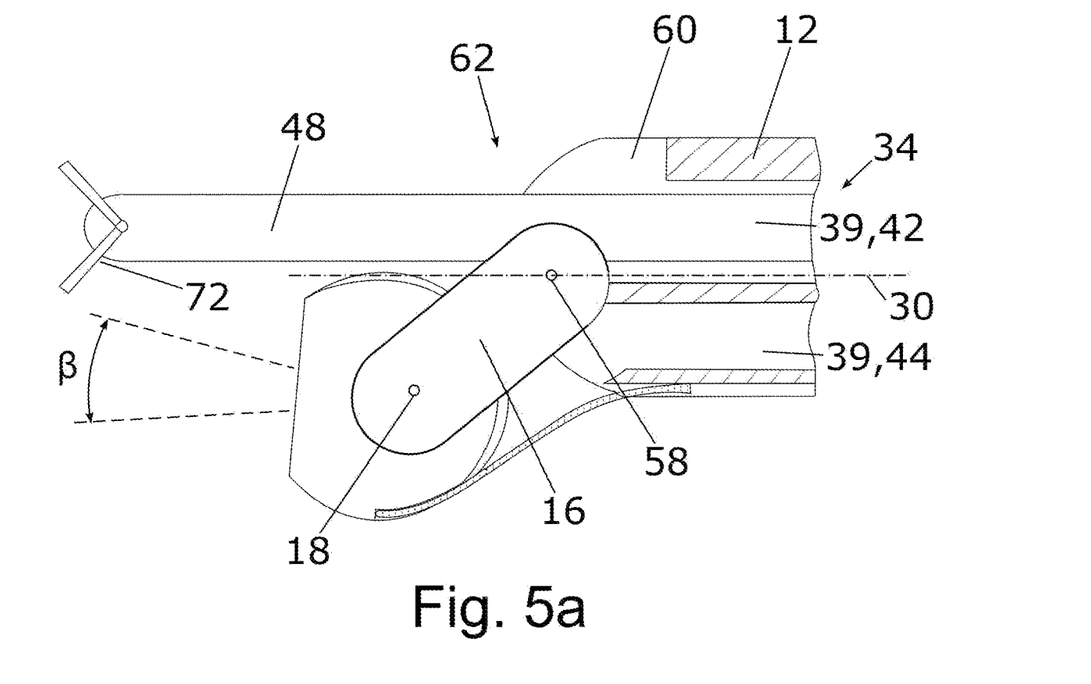

As illustrated in FIG. 5a, the work channel 34 can be designed to receive an instrument 48 and/or contain an instrument 48 as an alternative or in addition to the at least one second fluid line. This instrument 48 can have a tool 72, for example a cutting tool or a punching tool, at a distal end, which tool is adaptable for the respective medical operation.

Preferably, the shaft tube 12 is open in a section 60 on the upper side 62 such that an instrument 48, preferably a flexible instrument, is adjustable or bendable past the rotating drum 20 in a direction perpendicular to the longitudinal axis 30 of the shaft tube 12.

Figure 5B:
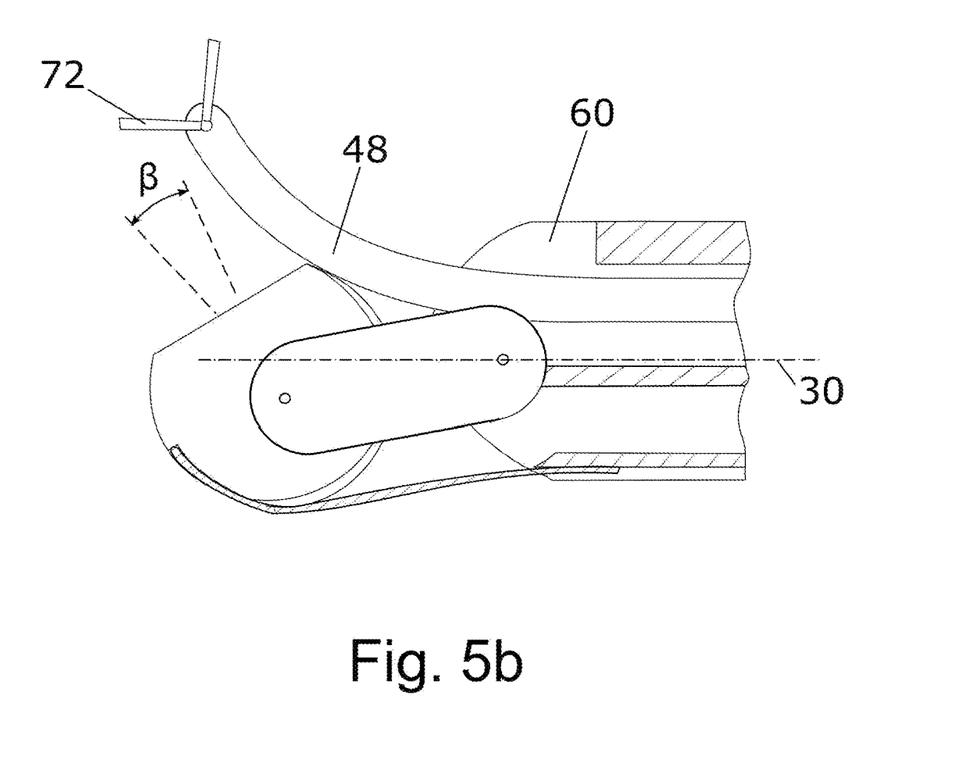
FIG. 5b: shows a longitudinal section of the endoscope as per FIG. 5a with the instrument in a bent state.

FIG. 5a shows a further preferred embodiment of the endoscope 10, in which the bearing fork 16 is fastened to the shaft tube 12 so as to be pivotable about a second axis of rotation 58 and the work channel 34 is open along the longitudinal axis 30 in a pivoted state of the bearing fork 16 so that preferably a rigid instrument 48 is able to be guided from the work channel 34 into the operation region. The bearing fork 16 is preferably controllable by means of a second control line, not illustrated, or another operating mechanism, preferably an operating mechanism for flexible shaft tubes as is known for example from US 2015/0359420 A1 cited at the outset. As illustrated in FIG. 5b, a flexible instrument 48, in particular, is adjustable with this pivotable bearing fork 16 by means of the rotating drum 20 in the direction of the upper open section 60. Thus, the tool 72 at the distal end of the instrument 48 can be moved into an operation region, with this tool 72 remaining in the field of view β of the imaging system 22 as a result of a simultaneous rotation of the rotating drum 20.

As an alternative or in addition thereto, the bearing fork 16 can also be connected to the shaft tube 12 by means of a flexible or elastically deformable element, preferably a rubber element, wherein the flexible element develops a passive restoring force in order to pivot the bearing fork 16 about the second axis of rotation 58 and open the work channel 34 for an instrument 48.

In addition to guiding the instrument 48, the work channel 34 can contain further channels for fluid guidance such that the rotating drum 20 is able to be cooled or cleaned and/or the operation region is able to be rinsed, even if an instrument 48 is used. Thus, the rinse of the operation region advantageously also acts to clean the instrument 48. By way of example, the work channel 34 to guide the instrument 48 can simultaneously be a liquid feed channel 41 and the shaft tube 12 can contain a further liquid extraction channel 44.

As illustrated in FIG. 6, the pivotable bearing fork 16 can reduce the bending radius of a flexible shaft tube 12, or increase the ability to be curved, even without an instrument, or can facilitate the bending radius of a rigid endoscope, for example in order to even capture a field of view of the imaging system 22 that is covered by the shaft tube 12 itself or in order to be able to see behind corners or obstacles. Thus, if the rotating drum 20 is rotated and the bearing fork 16 is rotated at the same time, the observation region is extended to an angle β' greater than 180° since the observation region is not restricted by the shaft tube 12 itself. The shaft tube 12 which is flexible at least in sections is configured as per FIG. 6 with a multiplicity of steering members 82 and is pivotable at an outer edge 84 of the steering members 82 by means of further control lines, not illustrated.

Figure 7A:
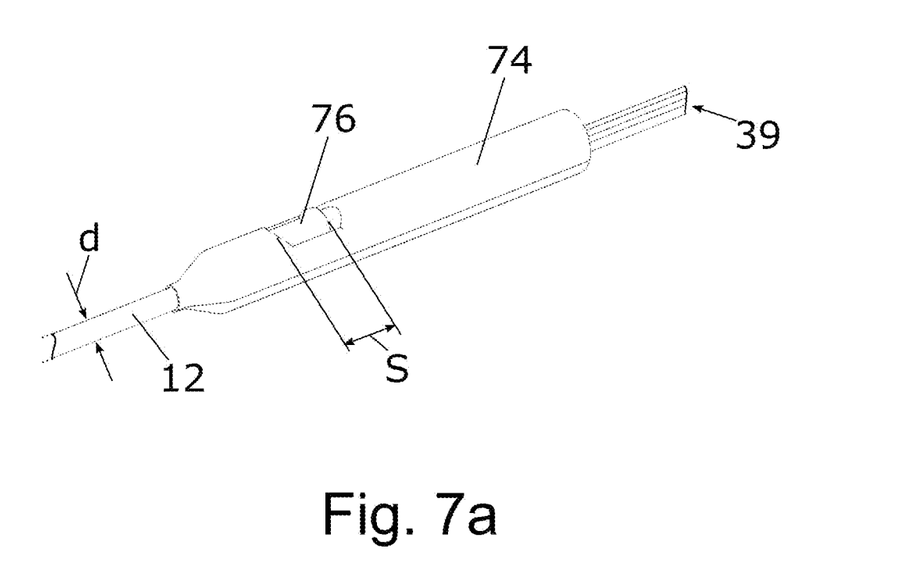
FIG. 7a: shows a perspective view of the endoscope as per FIG. 1a with a handle.
Figure 7B:
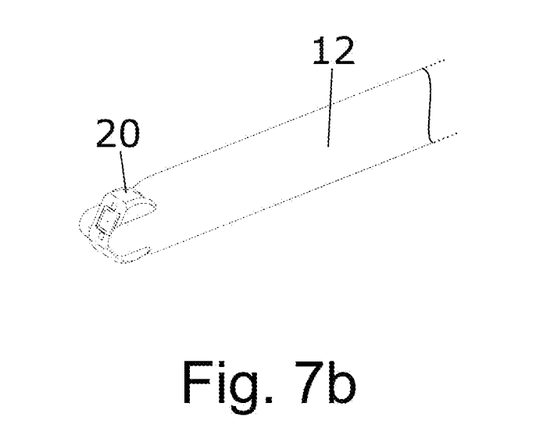

As illustrated in FIG. 7a, the at least one control line 32 is adjustable parallel to the longitudinal direction 30 of the shaft tube 12 by an operator by means of a handle 74 at a proximal end of the shaft tube 12 and a linearly displaceable operating element 76. The handle 74 preferably also transfers an electronic cable guidance to the flexible printed circuit board 68, which preferably as a control line 32 is linearly displaceable by an adjustment travel S in order to rotate the rotating drum 20 at the distal end 14 of the shaft tube 12 in FIG. 7b.

Preferably, the tool 72 of the instrument 48, as per FIG. 5a and FIG. 5b, is also operable by means of the handle 74.

The external diameter d of the shaft tube 12 is preferably 3 mm to 6 mm. Such a shaft tube 12 is suitable for a multiplicity of non-invasive medical operations in adult humans. Here, the bearing fork 16 is preferably rounded off at a distal end and the diameter of the rotating drum 20 preferably does not exceed this external diameter d in a direction perpendicular to the longitudinal axis 30 of the shaft tube 12 in order to minimize injury during medical use.

Preferably, when using a plurality of control lines 32, these are windable on different winding curves 38, not illustrated here, of the rotating drum 20, in particular at different distances a from the axis of rotation 30 in order to carry out different rotational adjustments through an angle α in the case of the same adjustment travel S of the control lines 32 in the longitudinal direction 30 of the shaft tube 12. These different winding curves 38 are also preferable if a small distance a is required but the supply line, in particular as a flexible printed circuit board 68, is limited by a maximum radius of curvature.

The invention also relates to a method for operating an above-described endoscope, wherein the rotating drum 20 is rotated through an angle α from an observation position as per FIG. 2b to a cleaning position as per FIG. 3a such that the imaging system 22 is aligned with the distal end 16 of the shaft tube 12 and the work channel 34, wherein in this position the at least one second fluid line 39 is used to rinse the imaging optical unit 26 and/or the illumination device 28. During the rinsing procedure, the rotating drum 20 can be pivoted in order, in particular, to clean the field of view β of the imaging system 22. For applications in which no rinsing fluid should penetrate into the operation region, in particular for a dry operation region, the rinsing fluid is preferably removed using a liquid extraction line 39, 44. Following the rinsing with the rinsing fluid, preferably a rinsing liquid, the rotating drum 20 can preferably be dried by means of an air flow from the air line 39, 40 before the rotating drum 20 is pivoted back into the observation position, preferably the previously departed observation position.

For a dry operation region in particular, it is alternatively often sufficient to clean an imaging optical unit that has steamed up as a result of humidity using an air flow. Here, the use of a rinsing liquid is advantageously not required.

Furthermore, the invention relates to a method for guiding an instrument 48 from the shaft tube 12, wherein the shaft tube 12, at least the distal end 14 of the shaft tube 12, is initially guided into an operation region. Subsequently, the rotating drum 20 is pivoted by means of the pivotable bearing fork 16 about a second axis of rotation 58, as per FIG. 5a, at least until the rotating drum 20 exposes the work channel 34 along a longitudinal axis 30 of the shaft tube 12. Then, the instrument 48 is pushed out of the work channel 34, in particular in the direction of an operation site. In a next step, the rotating drum 20 is pivoted by means of the control line 32 and about the first axis of rotation 18 in order to track and observe the instrument 48, in particular a tool 72, and the operation region with the field of view β of the imaging system 22. Especially for flexible instruments, the instrument 48 can be bent as per FIG. 5b by pivoting the bearing fork 16 about a second axis of rotation 58. In this method, the bearing fork 16 can be actively pivoted or the bearing fork 16 can be passively pivotable by means of a flexible or elastically deformable element as a result of a cooperation with the instrument.

LIST OF REFERENCE SIGNS

10 Endoscope
12 Shaft tube
14 Distal end of the shaft tube
16 Bearing fork
18 First axis of rotation
20 Rotating drum
22 Optical imaging system
24 Electronic image recorder
26 Imaging optical unit
28 Illumination device
30 Longitudinal axis of the shaft tube
32 At least one control line
34 Work channel
36 Outer side of the shaft tube
38 Winding curve
39 Second fluid line
40 Second air line
42 Liquid feed line
44 Liquid extraction line
46 Holes in the shaft tube
47 Opening in the shaft tube
48 Instrument
50 Recess
52 Protective collar
54 Reset means
55 Torsion spring
56 Bearing point of the rotating drum
58 Second axis of rotation
60 Open upper section of the shaft tube
62 Upper side of the shaft tube
63 Lower side of the shaft tube
64 Viewing direction of the imaging system
66 Flattened side of the rotating drum
68 Flexible printed circuit board as a control line
69 First fluid line
70 Depression on the rotating drum
71 Cable
72 Tool
74 Handle
76 Operating element
78 Bubble-shaped operation region
79 Tissue
80 Flow direction
82 Steering members
84 Outer edge of the steering members
a Distance between the first axis of rotation and the winding curve
d External diameter of the shaft tube
α Angle of the viewing direction of the imaging system
β Viewing angle or viewing field
β' Observation region
S Adjustment travel

I claim:

1. A method for operating an endoscope with a rotating drum or a rotation module, for use as a sterile disposable instrument, having an elongate rigid and/or flexible shaft tube which at a distal end mounts the rotating drum by means of a bearing fork, so as to be rotatable about at least one first axis of rotation, an optical imaging system being arranged in the rotating drum, the optical imaging system comprising an electronic image recorder and/or an imaging optical unit and/or an illumination device, with the at least one first axis of rotation running transversely to a longitudinal axis of the shaft tube and with the endoscope having at least one control line for rotating the rotating drum by way of a linear movement,
wherein the at least one control line of the rotating drum runs on an outer side/outer face of the shaft tube, so as not to restrict a work channel in an interior of the shaft tube and an internal diameter of the shaft tube, and is fastened to the rotating drum at at least one lever distance (a) from the at least one first axis of rotation,
wherein the at least one control line is subsequently being pulled or pushed in order to rotate the rotating drum, and
including the following steps:
guiding the shaft tube, at least with the distal end thereof, into an operation region,
pivoting a bearing fork about a second axis of rotation, at least until the rotating drum exposes the work channel along a longitudinal axis of the shaft tube,
guiding at least one instrument from the work channel into a medical operation region,
pivoting the rotating drum by means of the control line about the first axis of rotation in order to track the at least one instrument in the operation region with a field of view (β) of the imaging system,
pivoting the bearing fork about a second axis of rotation in order to move/bend the at least one instrument.

* * * * *